(12) United States Patent
Champion et al.

(10) Patent No.: US 11,433,138 B2
(45) Date of Patent: Sep. 6, 2022

(54) NANOCARRIERS AND INTRACELLULAR DELIVERY OF SAME

(71) Applicant: Georgia Tech Research Corporation, Atlanta, GA (US)

(72) Inventors: Julie Champion, Atlanta, GA (US); Sung In Lim, Atlanta, GA (US); Anshul Dhankher, Brooklyn, NY (US)

(73) Assignee: Georgia Tech Research Corporation, Atlanta, GA (US)

( * ) Notice: Subject to any disclaimer, the term of this patent is extended or adjusted under 35 U.S.C. 154(b) by 771 days.

(21) Appl. No.: 16/306,221

(22) PCT Filed: Jun. 7, 2017

(86) PCT No.: PCT/US2017/036331
§ 371 (c)(1),
(2) Date: Nov. 30, 2018

(87) PCT Pub. No.: WO2017/214261
PCT Pub. Date: Dec. 14, 2017

(65) Prior Publication Data
US 2019/0192679 A1 Jun. 27, 2019

Related U.S. Application Data

(60) Provisional application No. 62/346,702, filed on Jun. 7, 2016, provisional application No. 62/380,509, filed on Aug. 29, 2016.

(51) Int. Cl.
*A61K 47/64* (2017.01)
*A61K 47/65* (2017.01)
*A61K 39/385* (2006.01)
*A61K 9/127* (2006.01)
*A61K 47/69* (2017.01)
*A61K 47/62* (2017.01)
*C07K 16/18* (2006.01)
*A61K 47/68* (2017.01)
*A61K 31/713* (2006.01)

(52) U.S. Cl.
CPC .......... *A61K 47/6455* (2017.08); *A61K 9/127* (2013.01); *A61K 31/713* (2013.01); *A61K 39/385* (2013.01); *A61K 47/62* (2017.08); *A61K 47/65* (2017.08); *A61K 47/6849* (2017.08); *A61K 47/6919* (2017.08); *A61K 47/6929* (2017.08); *C07K 16/18* (2013.01)

(58) Field of Classification Search
CPC .... A61K 39/12; A61K 47/65; A61K 47/6929; A61K 2039/6093
USPC ..................... 435/6.1, 91.1, 91.31, 455, 458; 514/44 A, 44 R; 536/23.1, 24.5; 424/9.1
See application file for complete search history.

(56) References Cited

U.S. PATENT DOCUMENTS 8,580,274 B2 11/2013 Arakawa et al.
2012/0064110 A1* 3/2012 Ilyinskii ................. A61P 37/04
424/196.11

OTHER PUBLICATIONS

Bera et al (Protein & Peptide Letters, vol. 26, pp. 88-97 (2019)) (Year: 2019).*
Thomas et al (Agnew. Chem. Int. Ed., vol. 55, pp. 987-991 (2015)) (Year: 2015).*
Abraham et al (Scientific Reports, vol. 6, No. 21803, pp. 1-12 (Feb. 2016)) (Year: 2016).*
Efimov et al (Proteins: Structure, Function and Genetics, vol. 24, pp. 259-262 (1996)) (Year: 1996).*
International Search Report and Written Opinion from related application No. PCT/US2017/036331 dated Oct. 12, 2017 (13 pages).
Efimov, et al., "Crystallization and Preliminary Crystallographic Study of Pentamerizing Domain from Cartilage Oligomeric Matrix Protein: A Five-Stranded Alpha-helical Bundle," 1996 Proteins, 24(2): 259-62.
Kato, et al., "Model for the Complex Between Protein G and an Antibody Fc Fragment in Solution," Structure 1995 3(1):79-85.
Abraham, et al., "Intracellular Delivery of Antibodies by Chimeric Sesbania Mosaic Virus (SeMV) Virus Like Particles," Feb. 24, 2016 Sci Rep 6:21803.
Thomas, et al., "Controlling the Assembly of Coiled-Coil Peptide Nanotubes," Dec. 14, 2015 Angew Chem Int Ed Engl. Epub 55(3):987-91.

* cited by examiner

*Primary Examiner* — Jane J Zara
(74) *Attorney, Agent, or Firm* — Troutman Pepper Hamilton Sanders LLP; Ryan A. Schneider

(57) ABSTRACT

An embodiment of the present disclosure can include a nanocarrier for delivering a cargo to a cell comprising: a bundle domain and a binding domain, the binding domain configured to bind to the cargo. An embodiment of the present disclosure can include a method for delivering a cargo to a cell comprising: introducing an amino-acid based nanocarrier to the cell, the nanocarrier can comprise an alpha-helical protein bundle domain and a binding domain, the cargo can bound to the binding domain and the cargo can be therapeutic cargo.

13 Claims, 12 Drawing Sheets

NANOCARRIERS AND INTRACELLULAR DELIVERY OF SAME

CROSS-REFERENCE TO RELATED APPLICATIONS

This application claims the benefit of U.S. Provisional Patent Application Ser. No. 62/346,702, filed Jun. 7, 2016, entitled "Engineered Protein Nanocarriers For Intracellular Antibody Delivery," and U.S. Provisional Patent Application Ser. No. 62/380,509, filed Aug. 29, 2016, entitled "Multimeric Extracellular Antibody Carriers," the entire contents and substance of these applications are hereby incorporated by reference as if fully set forth below.

BACKGROUND

Protein engineering and recombinant technologies have created new classes of protein therapeutics with bioactivities not possible from small molecules. A particular success is antibodies, which have been engineered to bind a number of extracellular targets and are a significant and growing fraction of the protein therapeutics portfolio. These have shown incredible promise in the clinic for a variety of applications including inflammation, regenerative medicine, cancer, and autoimmune disease. Despite the successes of antibodies, the most notable exception from the current list is those with intracellular targets or function. The reason is not a lack of medical need. There is a significant list of "undruggable" targets, disease related protein-protein interactions that small molecules cannot block. The issue is not that antibodies cannot be found or engineered to bind these targets, as antibody engineering is a powerful tool and already many antibodies exist for intracellular targets but they are only used on fixed cells in laboratory immunostaining assays. The intrabody, an intracellularly expressed antibody, has been developed to target cellular components in live cells, but requires in vivo genetic manipulation and delivery for therapeutic applications. Arguably, the primary reason there are no intracellular antibody therapeutics is the significant, unmet challenge in delivering sufficient amounts of functional protein inside cells. Successful design and implementation of a functional intracellular antibody delivery system that is generally applicable to all antibodies would have significant impact on human health as it would open the door for a host of new antibody drug therapies to be realized for a wide variety of diseases.

BRIEF SUMMARY

An embodiment of the present disclosure can include a nanocarrier for delivering a cargo to a cell comprising: a bundle domain and a binding domain, the binding domain configured to bind to the cargo. In an embodiment, the bundle domain can be an alpha-helical protein. In an embodiment, the alpha-helical protein can comprise from about 2 to about 14 coils. In an embodiment, the alpha-helical protein can comprise 6 coils. In an embodiment, the binding domain can comprise a peptide. In an embodiment, the peptide can be selected from the group consisting of domain B of staphylococcal protein A (SPAB), domain C2 of streptococcal protein G (SPGC2), domain D of staphylococcal protein A (SPAD), domain C4 of peptostreptococcal protein L (PpLC4), and double-stranded RNA binding domain (DRBD). In am embodiment, the binding domain can be domain B of staphylococcal protein A (SPAB).

In an embodiment, the cargo can be bound to the binding domain. In an embodiment, the cargo can comprise a protein. In am embodiment, the cargo can be selected from the group consisting of an antibody, a siRNA molecule, and a DNA molecule. In an embodiment, the cargo can be an antibody. In an embodiment, the cargo can be immunoglobulin G (IgG). In an embodiment, the binding domain can be SPAB and the cargo can be IgG. In an embodiment, the binding domain can be DRBD and the cargo can be a siRNA molecule.

In an embodiment, the nanocarrier can comprise a linker. In am embodiment, an N-terminus of the linker can be bound to a C-terminus of the bundle domain, and a C-terminus of the linker can be bound to an N-terminus the binding domain. In an embodiment, an N-terminus of the linker can be bound to a C-terminus of the binding domain, and C-terminus of the linker can be bound to an N-terminus of the bundle domain.

In an embodiment, the linker can comprise an amino acid residue. In an embodiment, the linker can comprise a glycine residue, a serine residue, a proline residue, or mixtures thereof. In an embodiment, the linker can comprise from about 2 to about 30 amino acid residues. In an embodiment, the linker can comprise about 16 amino acid residues.

In an embodiment, the nanocarrier can comprise a delivery enhancer, the delivery enhancer can be configured to increase uptake of the cargo in the cell. In an embodiment, the delivery enhancer can be a peptide. In an embodiment, the delivery enhancer can be aurein or hexa-histidine.

In an embodiment, the nanocarrier can comprise a tag. In an embodiment, the tag can be selected from the group consisting of his-tag, glutathione-S-transferase tag, FLAG tag, and myc-tag. In an embodiment, the tag can be his-tag.

An embodiment of the present disclosure can include a method for delivering a cargo to a cell comprising: introducing an amino-acid based nanocarrier to the cell, the nanocarrier can comprise an alpha-helical protein bundle domain and a binding domain, the cargo can bound to the binding domain and the cargo can be a therapeutic cargo. In an embodiment, method can further comprise releasing the cargo from the binding domain into the cell.

An embodiment of the present disclosure can include a method making an assembled nanocarrier comprising: mixing a first nanocarrier monomer and a second nanocarrier monomer, the first nanocarrier monomer can comprise a first alpha-helical protein bundle domain and a first binding domain, the second nanocarrier monomer can comprise a second alpha-helical protein bundle domain and a second binding domain; unfolding the first and second alpha-helical protein bundle domains; coupling the first nanocarrier monomer and the second nanocarrier monomer to form an assembled nanocarrier.

In an embodiment, the first bundle domain and the second bundle domain can be the same. In an embodiment, the first bundle domain and the second bundle domain can be different. In an embodiment, the first binding domain and the second binding domain can be the same. In an embodiment, the first binding domain and the second binding domain can be different.

In an embodiment, the coupling can comprise self-assembly of the first and second alpha-helical protein bundle domains. In an embodiment, the unfolding can comprise introducing an unfolding agent selected from the group consisting of detergents, chaotropic salts, and alcohols. In an embodiment, the unfolding agent can be sodium dodecyl sulfate (SDS). In an embodiment, the method can further comprise refolding the first and second alpha-helical protein bundle domains. In an embodiment the refolding can comprise removing the unfolding agent.

DETAILED DESCRIPTION

Figure 1:
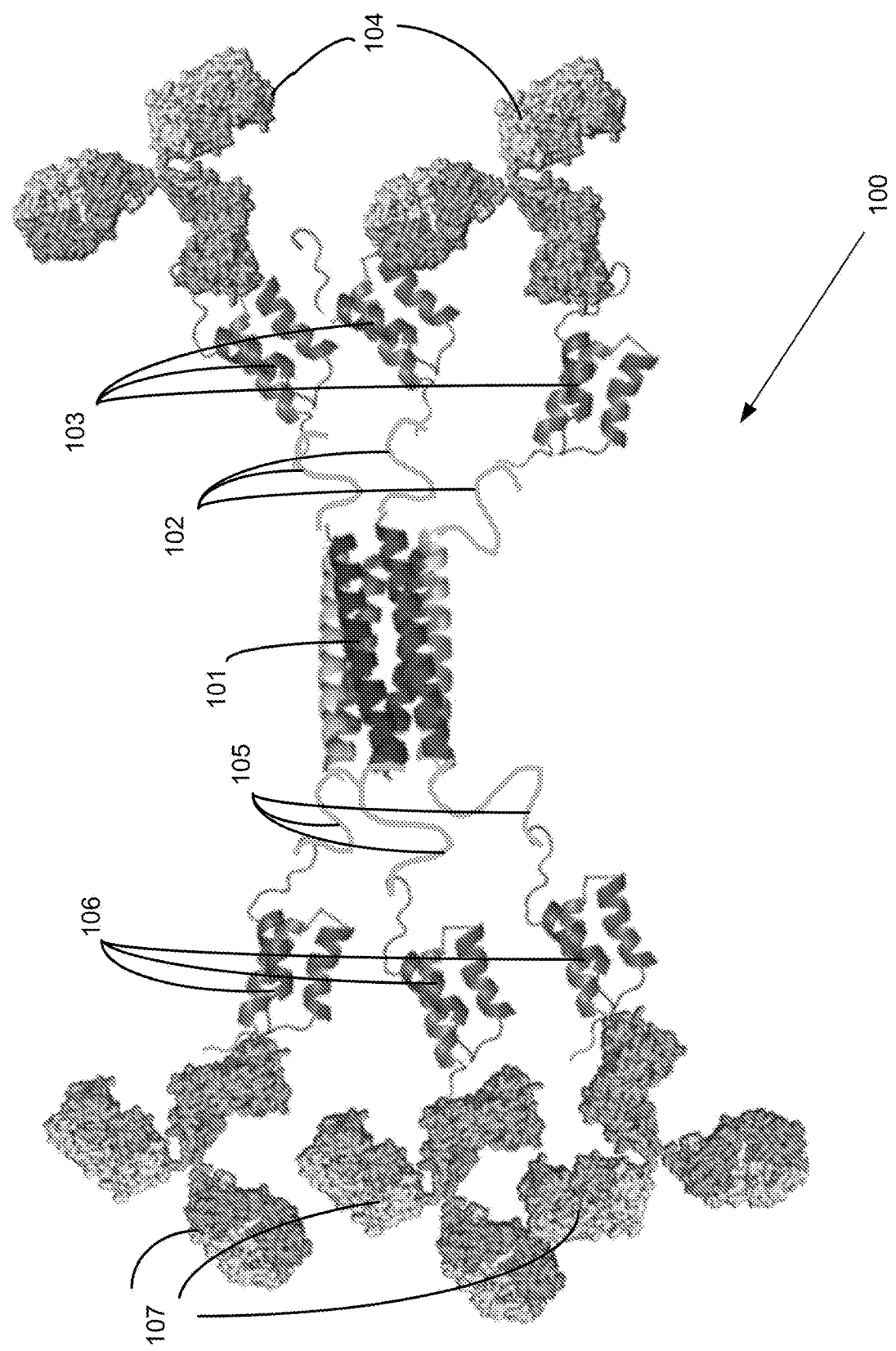
FIG. 1 illustrates a nanocarrier in accordance with one or more embodiments of the present disclosure.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

The disclosed nanocarriers represent a unique drug delivery platform for carrying and delivering a therapeutic cargo to a cell. In an embodiment, the nanocarriers can be fabricated completely from amino acids, peptides and proteins without the need for synthetic or other small molecules. One of ordinary skill in the art would understand that amino acids are the building blocks of peptides, proteins, and other biological molecules and thus, the nanocarriers may consist of amino acids, peptides, proteins, other biological molecules, or combinations thereof.

In an embodiment, the cargo can also consist of amino acids. In an embodiment, the cargo can be a biological molecule, such as a DNA or RNA. In an embodiment, the nanocarriers can be fabricated through mixing, self-assembly and other biological techniques without the need for chemistry or chemical modification. The nanocarriers can be capable of carrying any therapeutic cargo without any modification to the cargo itself. That is, the nanocarriers can have a binding domain with a specific binding affinity for a particular cargo. The nanocarriers can comprise binding domains that bind to the same cargo or can comprise multiple binding domains that are each specific to a different cargo, thus a single nanocarrier can be capable of delivering various types of cargo to the same site. The disclosed nanocarriers can be made up entirely of amino acids, proteins, and peptides and thus can advantageously be completely biocompatible (e.g., low to no cytotoxicity), easy-to-fabricate (e.g., modular, mix-and-go self-assembly), can achieve a very high cargo loading, and can be tumor-penetrable due to size.

FIG. 1 illustrates an exemplary embodiment of nanocarrier structure 100 comprising six separate nanocarrier monomers, each nanocarrier monomer comprising a bundle domain 101, a linker 102, 105 and binding domain 103, 106. FIG. 1 shows a non-limiting example of nanocarrier 100 wherein the nanocarrier 100 comprises six bundle monomers and five cargo 104, 107. However, nanocarriers comprising varying number of nanocarrier monomers and cargo are contemplated. That is, the number of bundle domains 101, linkers 102, 105, binding domains 103, 106, and cargo 104, 107 present in a single nanocarrier can vary. In an embodiment, the described nanocarrier comprises a bundle domain and a binding domain. Additionally nanocarrier can also comprise additional components such as a linker, a tag, delivery enhancer, and the like.

In an embodiment, an N-terminus end of the linker 102 can be bound to a C-terminus of the bundle domain 101, and a C-terminus of the linker 102 can be bound to an N-terminus the binding domain 103. In an embodiment, an N-terminus of the linker 105 can be bound to a C-terminus of the binding domain 106, and C-terminus of the linker 105 can be bound to an N-terminus of the bundle domain 101.

In an embodiment, the nanocarrier can be a nanocarrier for delivering a cargo, e.g., a therapeutic cargo, to a cell. The nanocarrier can comprise a bundle domain and a binding domain.

In an embodiment, the bundle domain can be a protein, such as an alpha-helical protein. The alpha-helical protein can comprise any number of coils. For example, the alpha-helical protein can comprise from about 2 to about 14 coils. The alpha-helical protein can be a HEX protein, or a protein comprising 6 coils. The coils in a bundle may be the same, or the coils in the bundle may be different. The bundle can comprise long coils or short coils such that the aspect ratio and dimensions of the bundle can depend on the number of coils that make it and the length of those coils. One of ordinary skill in the art would understand what is considered to be short coils or long coils. The bundles may be responsive to stimuli, for example disassembling at lower pH (such as that of an intracellular endosome). The coils may also be responsive to other stimuli such as temperature and salt concentration. The bundle domain can be heat stable, e.g., stable up to about 60° C., and acid-stable, e.g., stable down to a pH of about 4. While not wishing to be bound by theory, it is thought that the bundle domain serves as a stable core from which to recombinantly attach cargo binding domains.

In an embodiment, the binding domain can be configured to bind to the cargo. As such, the binding domain can exhibit a particular binding affinity for certain cargo, e.g., an antibody, an siRNA, or the like. The binding domain can bind to the cargo without the need for covalent bonds. In an embodiment, the binding domain can be configured to exhibit a binding affinity to the cargo such that the cargo can stay bound to the nanocarrier in the blood stream. In an embodiment, the binding domain can be configured to exhibit a binding affinity to the cargo such that the cargo can stay bound to the nanocarrier in the blood stream but can be released from the nanocarrier in the cell. In an embodiment, the binding domain can consist of amino acids, e.g., peptides, proteins, and the like. In an embodiment, the binding domain comprises a peptide.

In an embodiment, the binding domain can be a binding domain configured to bind to an antibody, e.g., IgG. In an embodiment, the binding domain can be a naturally occurring IgG binding protein found in bacteria. In an embodiment, the Fc domain of IgG can be bound to the binding domain because it is away from the antigen binding site. In an embodiment, the binding domain can be domain B of staphylococcal protein A (SPAB), domain C2 of streptococcal protein G (SPGC2), domain D of staphylococcal protein A (SPAD), domain C4 of peptostreptococcal protein L (PpLC4), or combinations thereof. The binding domain can bind the top of the heavy chain or the light chain. The binding domain can also be a human Fc receptor that naturally binds the Fc domain of IgG. In an embodiment, the binding domain can be an Fc binding domain of Fc receptors, including, but not limited to, all of the Fc gamma receptors and FcRN.

In an embodiment, the binding domain can be configured to bind to siRNA. For instance, the binding domain can be double stranded RNA binding domain (DRBD). In an embodiment, the binding domain can be a peptide that is configured to bind to DNA. The peptide can be either non-sequence specific or sequence specific.

In an embodiment, the nanocarrier does not include a binding domain. For instance, the cargo can be direct fused to the linker, or to the bundle domain.

In an embodiment, the linker can comprise amino acids. In an embodiment, the linker can consist of only amino acids. In an embodiment, the linker can comprise repeat units of amino acids selected from the group consisting of glycine, serine, and proline. In an embodiment, the linker can comprise unstructured or unstructured repeats of glycine and serine. In an embodiment, the linker can comprise repeats of glycine, serine, and proline. One of ordinary skill in the art would appreciate that various combinations of repeat units would yield more flexible or stiffer linkers. Thus, the linker can be a flexible linker or a stiff linker. The linkers can comprise about 2 to about 30 amino acids, about 2 to about 20 amino acids, about 2 to about 12 amino acids, about 5 to about 30 amino acids, about 5 to about 20 amino acids, about 5 to about 15 amine acids, about 5 to about 10 amino acids, or about 10 to about 16 amino acids. In an embodiment, the linker can comprise about 16 amino acids.

In an embodiment, the linker can be structured, including, but not limited to, alpha-helical linkers. While not wishing to be bound by theory, it is believed that the linkers generally serve to spatially separate different nanocarrier components or domains, for example, the bundle domain and the binding domain. However, the linker can increase the size and flexibility of the protein, which can affect its function in vivo and in cells.

In an embodiment, the linker can be "functional". For example, it can be made to be cleaved by proteases. For instance, in a non-limiting example, an intracellular protease cleavage site can be imbedded in the linker, and the antibody can be released from the bundle domain upon exposure to the protease. Linkers can also affect protein expression.

In an embodiment, the nanocarrier can comprise a delivery enhancer configured to increase uptake of cargo in the cell. For instance, the delivery enhancer can increase cell uptake or escape for the intracellular endosome (e.g., to get to the cytosol). In an embodiment, the binding domain can be modified to comprise a delivery enhancer, e.g., a cell penetrating or endosomal escape peptide or protein configured increase delivery of cargo to the cytosol. The delivery enhancer can be located on or between various components of the nanocarrier. For example, the delivery enhancer can be bound to the binding domain and to a linker, or the delivery enhancer can be bound to the bundle domain and to a linker, and the like. In an embodiment, the delivery enhancer can comprise aurein. In an embodiment, the delivery enhancer can comprise hexa-histidine (e.g, 6 histadines, for a total of 36 on the nanocarrier). Other non-limiting examples of nanocarriers can be cationic peptides, e.g., TAT from HIV, or octa-arginine or octa-lysine, and amphipathic peptides including, but not limited to primary amphipathic peptides like Pep-1 from simian virus and HIV, beta-sheet amphipathic peptides like MPG from simian virus and HIV, and alpha-helical amphipathic peptides, e.g., INF from influenza. A wide range of delivery enhancers are contemplated for use in the disclosed nanocarriers. For instance, the delivery enhancer can comprise peptides that can be derived from or based on designs from viral pathogens, including, but not limited to, the sweet arrow peptide and derivatives. In an embodiment, the delivery enhancer can comprise an amphibian microbial peptide. In an embodiment, the delivery enhancer can comprise aurein, magainin 2, buforin 2, or combinations thereof.

In an embodiment, the nanocarrier can comprise a tag configured to increase solubility of the nanocarrier. In an embodiment, the tag can be used for purification. In an embodiment, the tag can be a his-tag. In an embodiment, the tag can be a his-tag, glutathione-S-transferase tag, FLAG tag, myc-tag, or combinations thereof.

In an embodiment, the nanocarrier can be configured to deliver a cargo to a cell. For instance the nanocarrier can be configured to deliver a therapeutic cargo to a cell. In an embodiment, the cargo can be a biological molecule. In an embodiment, the cargo can be an antibody, including, but not limited to immunoglobulin G (IgG). Without wishing to be bound by theory, it is believed that the Fc domain provides a particular advantage for binding to the carrier because it is spatially located away from the antigen binding site. In an embodiment, the cargo can be an RNA molecule, such as siRNA. In a embodiment, the cargo can be a DNA molecule. In an embodiment, the cargo can be any other therapeutic peptide or protein. In an embodiment, the cargo can be a small molecule drug.

Figure 2:
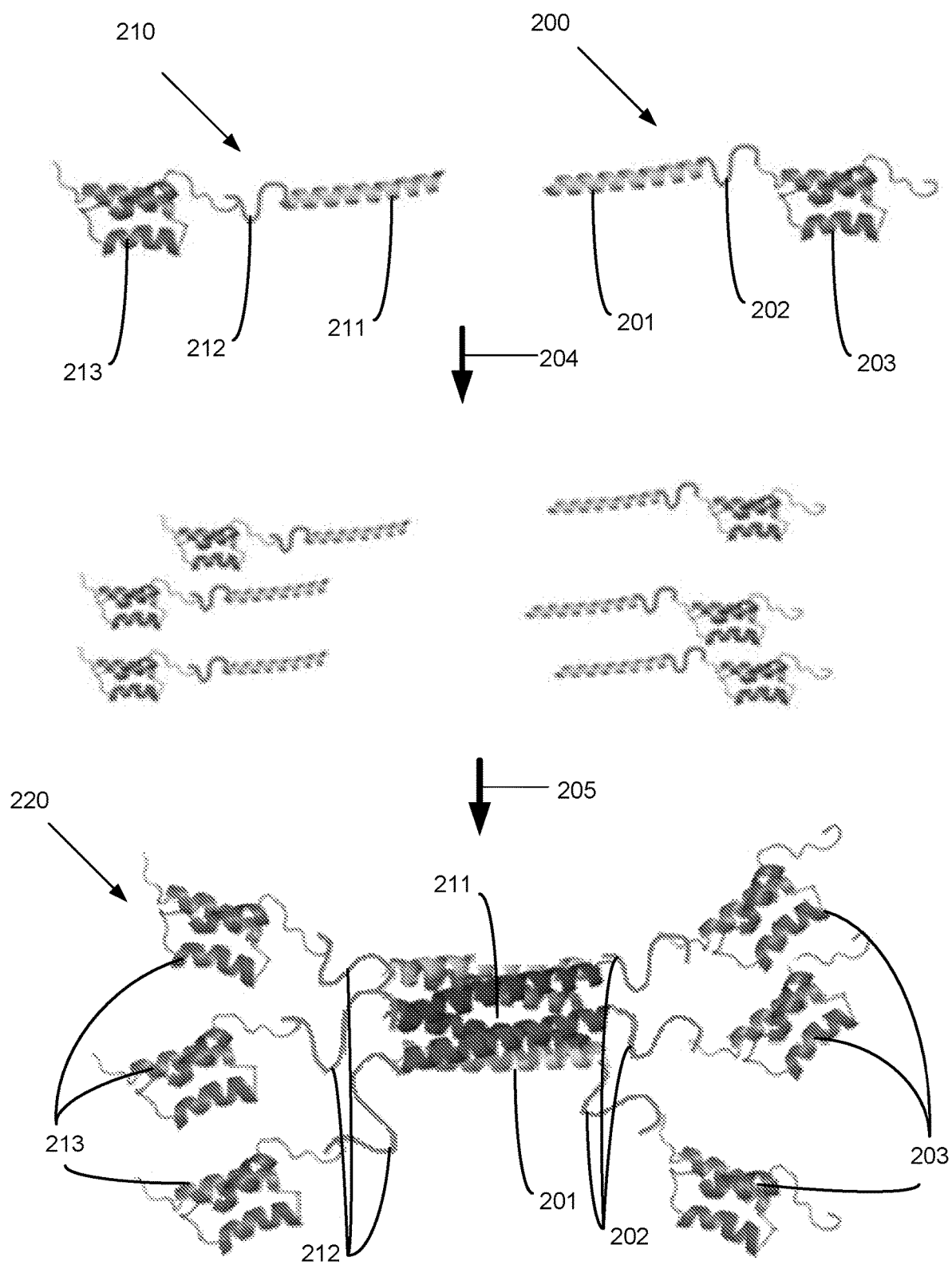
FIG. 2 illustrates a method of producing a nanocarrier in accordance with one or more embodiments of the disclosure.

FIG. 2 illustrates an exemplary method of making the disclosed nanocarrier structure 220. The method can comprise mixing a first nanocarrier monomer 200 and a second nanocarrier monomer 210. The first nanocarrier monomer 200 can comprise a first bundle domain 201 and a first binding domain 203. The first nanocarrier monomer 200 can further comprise first linker 202. The first nanocarrier monomer 210 can comprise a second bundle domain 211 and a second binding domain 213. The second nanocarrier monomer 210 can further comprise second linker 212. The method can further comprise an unfolding step 204. The unfolding 204 can comprise unfolding the first bundle domain 201 and the second bundle domain 210. The unfolding can comprise introducing an unfolding agent. The unfolding agent can be any agent that promotes unfolding of the bundle domain, including, but not limited to detergents, chaotropic salts, and alcohols. In an embodiment, the unfolding agent comprises sodium dodecyl sulfate (SDS). The unfolding agent can be a detergent, including, but not limited to, SDS, Triton X-100, and sodium deoxycholate. The unfolding agent can be a chaotropic salt, including, but not limited to, urea, guanidinium hydrochloride, lithium perchlorate, guanidine thiocyanate. The unfolding agent can be an alcohol, including but not limited to short-chain alcohols, e.g., methanol, ethanol, and the like. The unfolding step 204 can also comprise heating, raising pH, e.g., with sodium bicarbonate, or lowering pH, e.g., with acetic acid.

The method can further comprise a coupling step 205. The coupling 205 can comprise coupling the first nanocarrier monomer 200 and the second nanocarrier monomer 210 to form assembled nanocarrier 220. Coupling 205 can comprise refolding the first bundle domain 201 and the second bundle domain 210. Coupling 205 can comprise self-assembly of the first bundle domain 201 and the second bundle domain 210 to form assembled nanocarrier 220. The refolding step can comprise removing or reversing the unfolding agent.

The method can further comprise loading the cargo into or onto the nanocarrier. The loading step can comprise mixing the cargo with the assembled nanocarrier such that the cargo binds to the binding domain.

Each component of the nanocarrier (e.g., each bundle domain, binding domain, linker, delivery enhancer, cargo, tag, etc.) can be the same, or different. For instance, in an embodiment, the bundle domains of the nanocarrier can be the same, or homo-bundle domains. In an embodiment, the bundle domains of the nanocarriers can be different, or hetero-bundle domains. Likewise, in an embodiment the binding domains of the nanocarrier can be the same. In an embodiment, the binding domains of the nanocarriers can be different.

In an embodiment, the linkers of the nanocarrier can be the same. In an embodiment, the linkers of the nanocarriers can be different. Likewise, in an embodiment, the delivery enhancers of the nanocarrier can be the same. In an embodiment, the delivery enhancers of the nanocarriers can be different.

The type of cargo can be based on the type of binding domain present in the nanocarrier. That is, the binding domain can be configured to bind to a specific type of cargo. For instance, if the nanocarrier comprises various binding domains, then various types of cargo can be bound to the nanocarrier at those binding domains.

An embodiment of the invention can be a method for delivering a cargo, such as a therapeutic cargo, to a cell. The method can comprise introducing an amino-acid based nanocarrier to the cell. The nanocarriers contemplated for in vivo and in vitro applications. That is, the nanocarrier can be introduced to a subject, such as a human. The nanocarrier can comprise a bundle domain and a binding domain, wherein the cargo can be bound to the binding domain and wherein the cargo can be a therapeutic cargo. The method can further comprise releasing the cargo from the binding domain into the cell. In an embodiment, the method can comprise delivering the cargo to the cell by introducing the entire nanocarrier to the cell, wherein the cargo is not released from the binding domain or the nanocarrier.

EXAMPLES

Example 1 Cloning and Expression of Fusion Peptides

The gene construct encoding components of an exemplary nanocarrier: either H6-SPAB-Hex or Hex-SPAB-H6 was subcloned into an IPTG-inducible bacterial expression vector pQE80, yielding pQE80-SPAB-Hex and pQE80-Hex-SPAB, respectively. The bacterial expression host, *Escherichia coli* TOP10, was transformed with the pQE80-SPAB-Hex or pQE80-Hex-SPAB, and was grown in 2×YT medium at 37° C. Protein expression was induced by 1 mM IPTG when the OD reached 0.6, and continued for 5 h. After collecting cells by centrifugation, proteins were purified by Ni-NTA affinity chromatography under native conditions according to the manufacturer's instruction. For expression of the Au-Hex nanocarrier, the restriction-free cloning method was used to insert the Aurein 1.2 domain N-terminally and C-terminally to pQE-Hex-SPAB and pQE-SPAB-Hex, respectively. A vector encoding H6-SPAB-Hex-TAT-HA2 was similarly constructed. Transformation, expression and protein purification were performed in the same way as described above.

Figure 3:
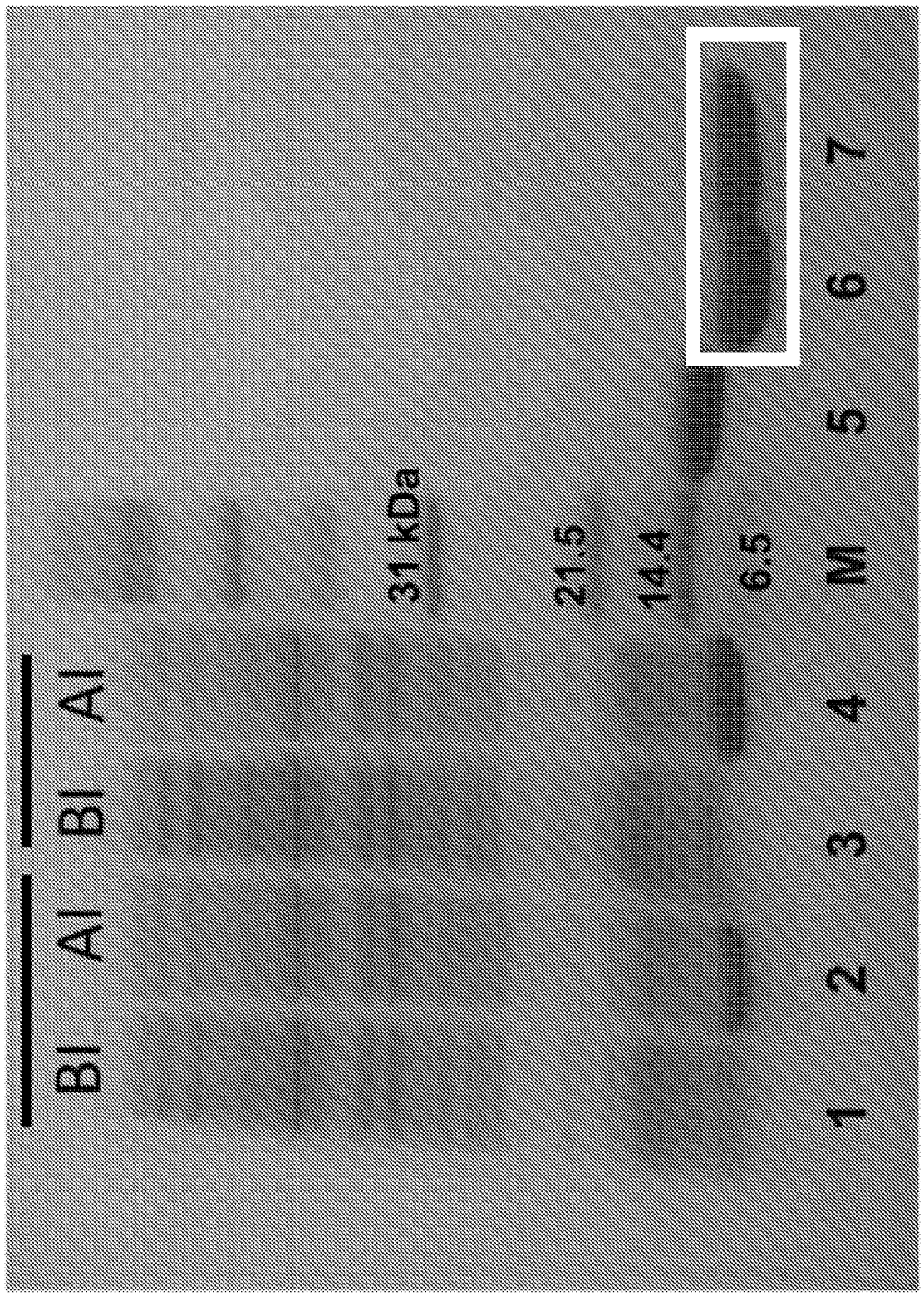
FIG. 3 illustrates an SDS page gel of protein expression for fusion proteins in accordance with one or more exemplary embodiments of the disclosure.

As shown in FIG. 3 a stained SDS-PAGE gel was used to visualize expression of H6-SPAB-Hex (lane 2) or Hex- SPAB-H6 (lane 4) and purification of the respective fusion proteins (lanes 6 and 7). An example protein, lysozyme, was used in lane 5.

Example 2 Generation of Nanocarrier

Sodium dodecyl sulfate (SDS) was added to a final concentration of 0.2% (w/v) to a 1:1 M ratio mixture of purified H6-SPAB-Hex (1.5 mg/mL) and Hex-SPAB-H6 (1.5 mg/mL) in PBS. After 10 min, the mixture was buffer-exchanged to PBS using a PD-10 desalting column. The resulting Hex nanocarrier can be concentrated using Vivaspin centrifugal filters.

Example 3 Cell Culture

HeLa cells were seeded onto a 96-well plate at a density of 5000 cells per well in 100 µL DMEM supplemented with 10% (v/v) fetal bovine serum (FBS) and antibiotics (100 µg/mL penicillin and 50 µg/mL streptomycin), and incubated overnight for attachment at 37° C. under humidified air containing 5% (v/v) CO2. The medium was replaced with 100 µL fresh medium containing a protein(s) of interest at appropriate concentrations and/or molar ratios.

Example 4 Binding Affinity of Hex Nanocarrier towards IgG

Biotinylated IgG was immobilized onto optical biosensors to enable high throughput kinetic analyses in microplate format. The IgG-binding behavior to the Hex nanocarrier in comparison to soluble SPAB at neutral and acidic pH was assessed. Soluble SPAB displayed nanomolar affinities towards mouse IgG ($IgG_M$), with a 17-fold stronger binding at neutral pH compared to pH 5.0 (Table 1). On the other hand, the binding between the Hex nanocarrier and $IgG_M$ at neutral pH was so strong that KD was below picomolar concentration, which is the lower limit detectable by the system. At pH 5.0, the binding became weaker with $K_D$ of 5.14 nM, but was still stronger by >91-fold in comparison to the interaction between SPAB and $IgG_M$. A similar trend was observed in the binding assay using rabbit IgG ($IgG_R$).

C. under humidified air containing 5% (v/v) $CO_2$. The Hex nanocarrier and the labeled IgG were mixed at appropriate molar ratios and concentrations in 100 µL of fresh supplemented medium, left to stand for 10 min at RT, and then used to replace the old medium. At appropriate time points, cells were washed three times with PBS, and then imaged by an Axio Observer Z1 fluorescence microscope or a LSM 700 confocal laser scanning microscope (Carl Zeiss, Germany). For flow cytometry, cells were harvested with 0.2% trypsin-EDTA, and then counted with an Accuri C6 flow cytometer (BD Biosciences, San Jose, Calif.) using the FL2 channel (λex=488 nm, λem=540/20 nm). Accuri CFlow software was used for analysis.

$IgG_M$-TAM or $IgG_R$-TAM at the fixed concentration of 0.6 µM was mixed with the Hex nanocarrier at various molar ratios of 1:0, 1:1, 3:1, 6:1 IgG-TAM:Hex. The cellular fluorescence was increasingly pronounced with higher $IgG_R$ loading density while the inverse correlation was observed with $IgG_M$.

Figure 4:
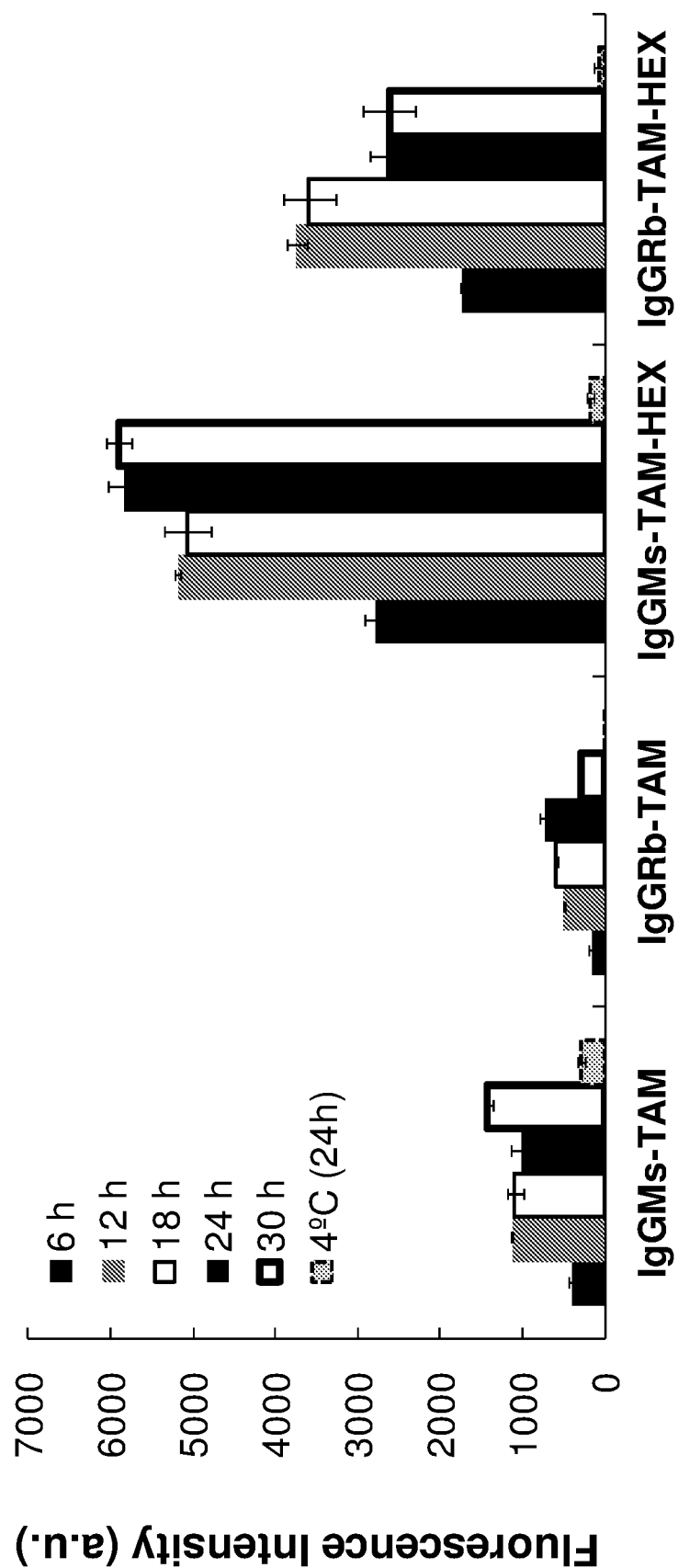
FIG. 4 illustrates a graph of fluorescence intensity at different time points using antibodies labeled with fluorescent TAM (IgG-TAM) or antibodies labeled with TAM which are bound to a nanocarrier (IgG-TAM-HEX) in accordance with an exemplary embodiment of the disclosure.

As shown in FIG. 4 fluorescence intensity measured by flow cytometry demonstrates intracellular delivery of either mouse IgG (IgGM) or rabbit IgG (IgGRb) when mixed with HEX nanocarrier. In the absence of HEX nanocarrier delivery is negligible.

Figure 5:
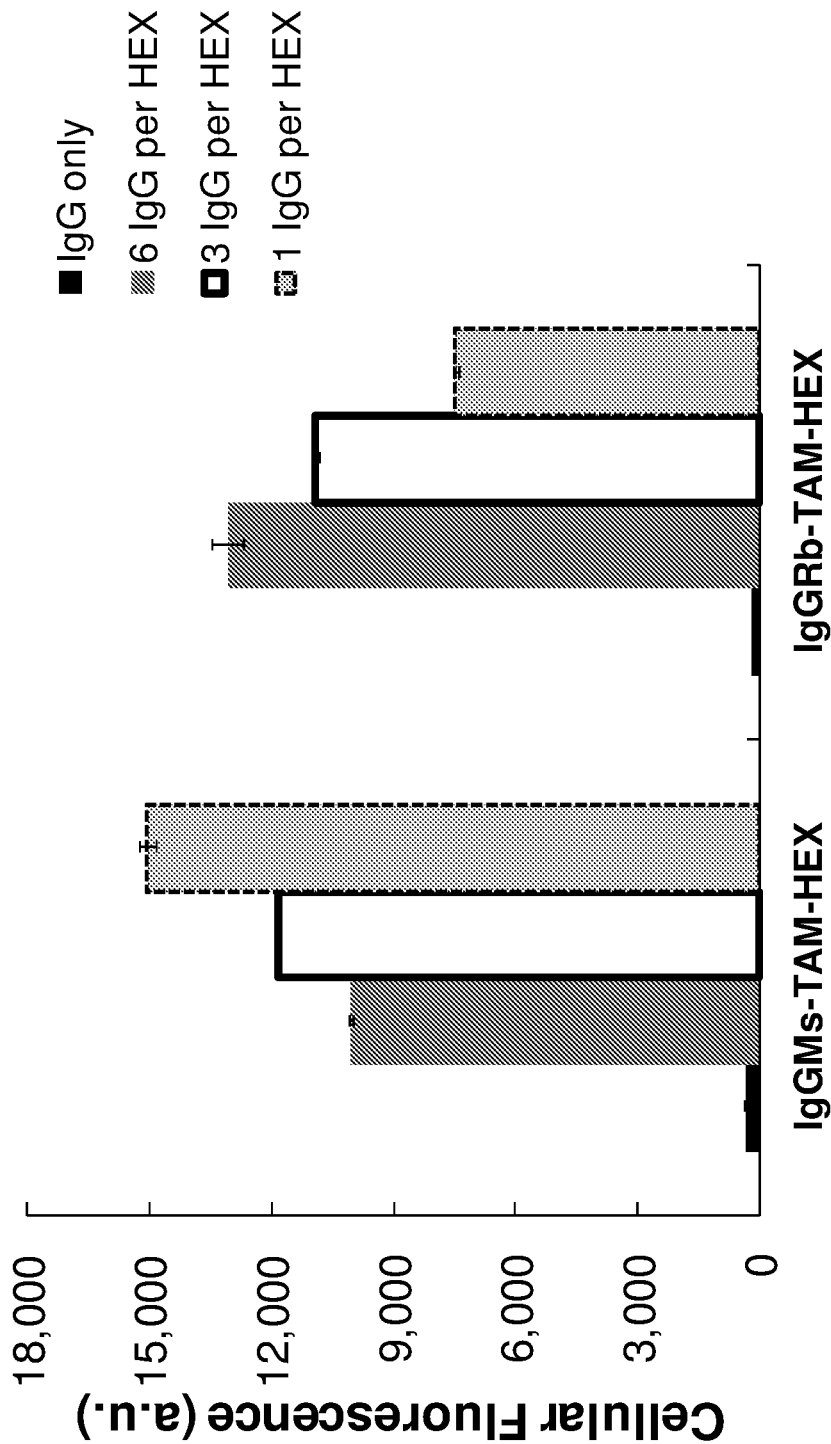
FIG. 5 illustrates a graph of cellular fluorescence using antibodies labeled with TAM which are bound to a nanocarrier at different ratios of antibody (IgG) to nanocarrier (HEX) in accordance with an exemplary embodiment of the disclosure.

As shown in FIG. 5 fluorescence intensity measured by flow cytometry demonstrates intracellular delivery of either IgGM or IgGRb at various molar ratios 1:0 (IgG only), 6:1, 3:1, and 1:1. In the absence of HEX nanocarrier delivery is negligible.

Figure 6:
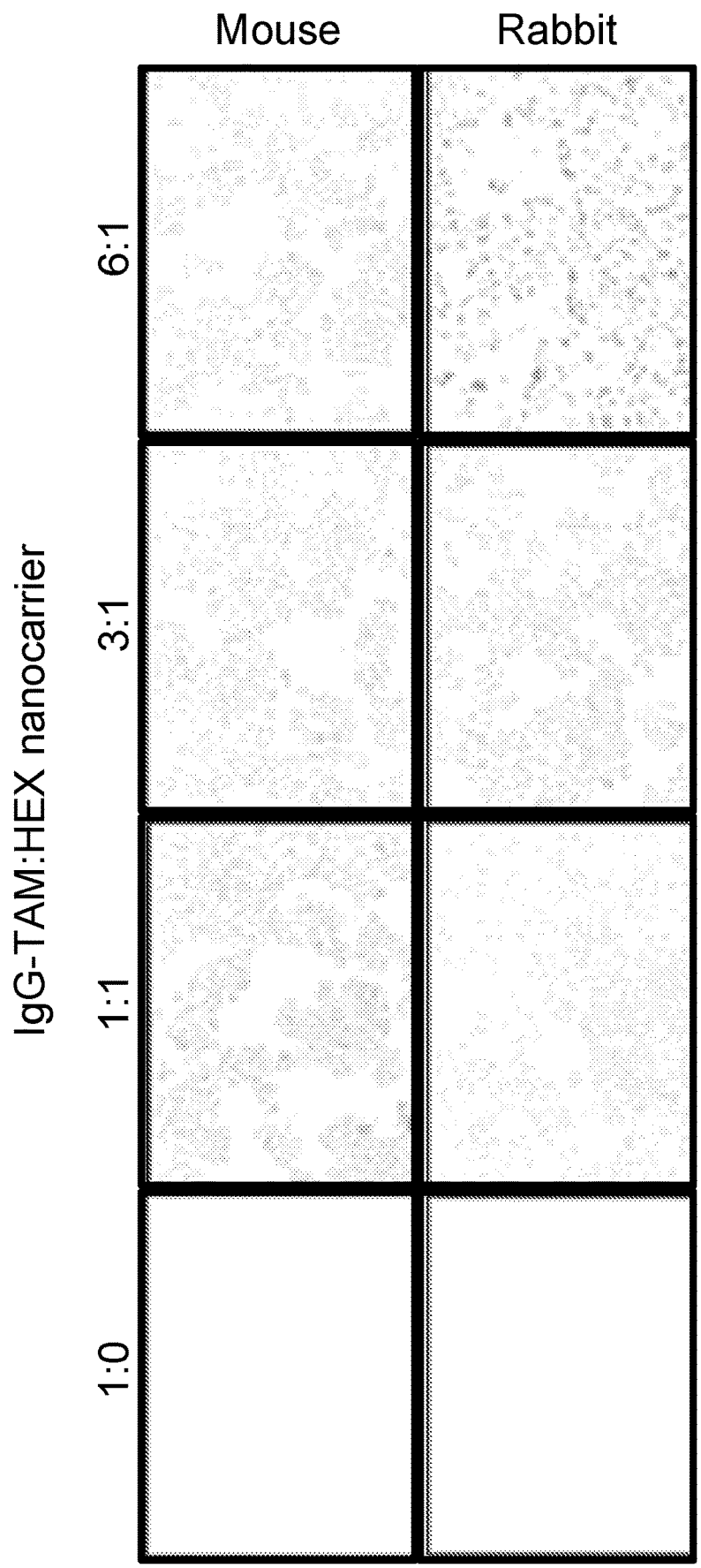
FIG. 6 illustrates microscopy fluorescence images demonstrating delivery of rabbit or mouse antibodies labeled with TAM bound to HEX nanocarrier at varying ratios of labeled antibody (IgG-TAM) to HEX nanocarrier.

As shown in FIG. 6 TAMRA-labeled $IgG_M$ or $IgG_R$ at 0.6 µM was mixed with HEX nanocarrier at various molar ratios of 1:0, 1:1, 3:1, and 6:1 IgG-TAM:Hex, and then incubated with HeLa cells for 24 h. Cellular fluorescence was imaged by fluorescence microscopy.

Example 6 Intracellular Delivery of Anti-Beta Tubulin r Anti-NPC Antibody by the Hex Nanocarrier HeLa cells were plated and cultured as described above. Anti-tubulin antibody or anti-nuclear pore complex antibody

TABLE 1

| IgG subtype | Antigen | pH 7.4 | | | pH 5.0 | | |
|---|---|---|---|---|---|---|---|
| | | $k_{on} \times 10^5$ (s$^2$) | $k_{off} \times 10^5$ (M$^2$s$^2$) | $K_D$ (nM) | kon × 10$^5$ (s$^2$) | $k_{off} \times 10^5$ (M$^2$s$^2$) | $K_D$ (nM) |
| $IgG_M$ | SPAB | 2.06 ± 0.20 | 5.82 ± 0.07 | 28.3 ± 2.8 | 0.084 ± 0.003 | 3.94 ± 0.06 | 470 ± 19 |
| | Hex | 1.51 ± 0.01 | <10$^{-4}$ | <10$^{-3}$ | 2.20 ± 0.04 | 1.13 ± 0.01 | 5.14 ± 0.12 |
| $IgG_R$ | SPAB | 1.59 ± 0.06 | 8.42 ± 0.06 | 53 ± 2 | 0.14 ± 0.09 | 3.57 ± 0.04 | 255 ± 17 |
| | Hex | 1.95 ± 0.02 | <10$^{-4}$ | <10$^{-3}$ | 3.11 ± 0.06 | 0.43 ± 0.00 | 1.39 ± 0.03 |

Example 5 Intracellular Delivery of Fluorescently Labeled Antibody by a Nanocarrier Mouse or rabbit IgG dissolved in PBS (pH 8.5) at the concentration of 7 mg/mL (47 µM) was mixed with a 10-fold molar excess of TAMRA-NHS at RT for 1 h, and then desalted using a PD-10 column to remove residual dye. HeLa cells were plated at on a glass bottom dish at a density of 5000 cells per cm$^2$ for microscopy or a 48-well microplate at a density of 4×104 cells per well for flow cytometry in DMEM supplemented with 10% (v/v) fetal bovine serum (FBS) and antibiotics (100 µg/mL penicillin and 50 mg/mL streptomycin), and incubated overnight for attachment at 37° was mixed with the Hex nanocarrier, and then incubated with cells in the same way. At 24 h post-incubation, cells were washed three times with PBS, and then fixed with 4% (v/v) paraformaldehyde at RT for 10 min. After washing cells three times with PBS, cells were permeabilized in a solution consisting of 0.25% (v/v) Triton X-100 and 2% (w/v) bovine serum albumin (BSA) in PBS at RT for 5 min. After washing, cells were incubated in blocking solution consisting of 2% (w/v) BSA in PBS at RT for 1 h to inhibit non-specific immunostaining, and then treated with goat anti-mouse IgG Alexa Fluor 647 and Hoechst 33,342 at RT for 1 h to visualize intracellularly delivered antibodies and the nucleus, respectively. Microscopy images were obtained by a LSM 700 confocal microscope or an Axio Observer Z1 microscope.

Figure 7:
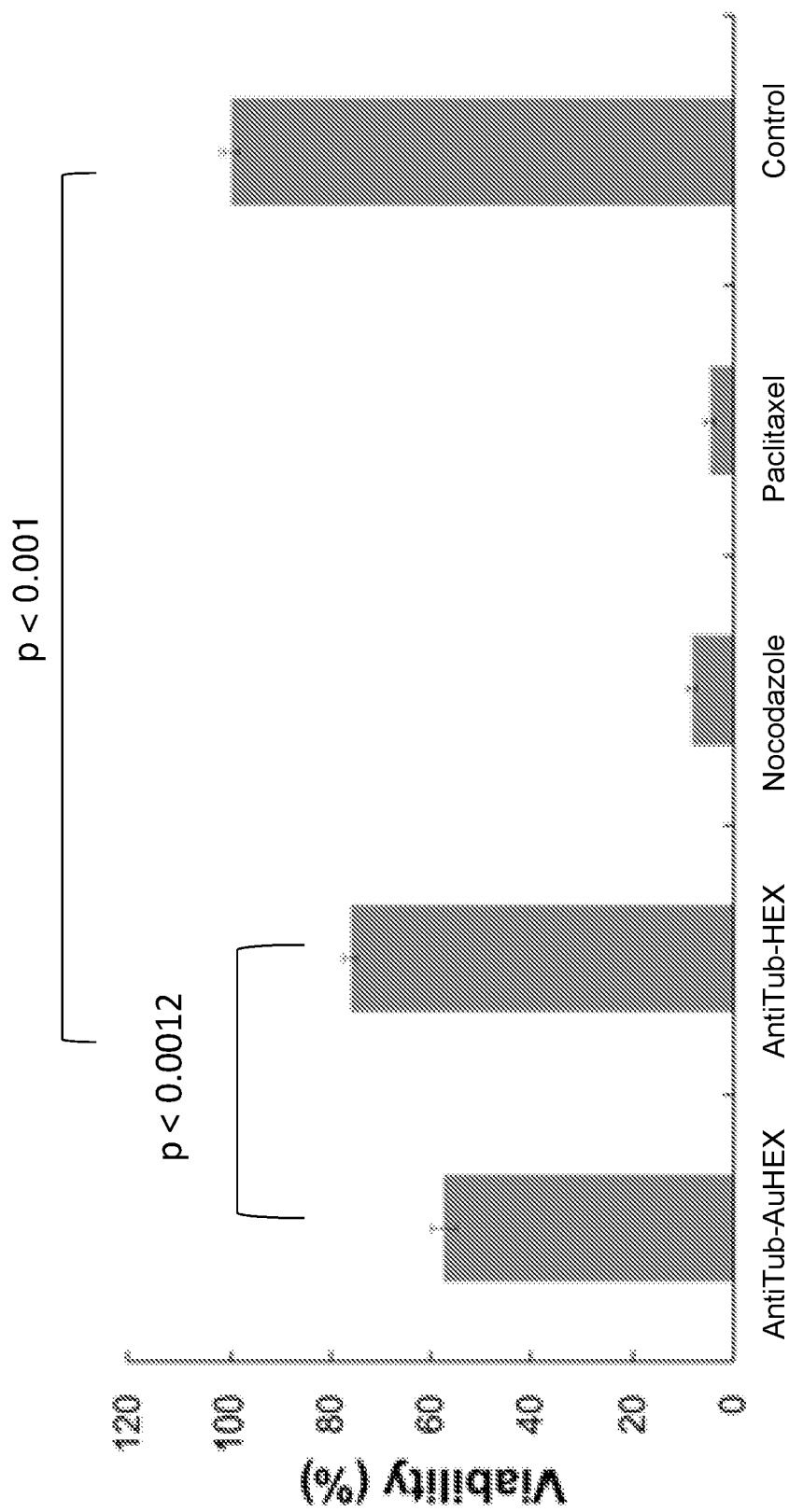
FIG. 7 illustrates a graph of cell viability under varying conditions. AntiTub-AuHEX and AntiTub-HEX demonstrate cell viability under conditions using an anti-tubulin antibody (AntiTub) which is bound to a nanocarrier (AuHEX or HEX) in accordance with one or more exemplary embodiments of the disclosure.

As shown in FIG. 7 Cell viability of HeLa cells incubated for 48 h with 0.2 or 0.4 µM of IgGM or anti-beta tubulin antibody mixed with the Hex nanocarrier at a fixed molar ratio of 3:1 IgG:Hex was normalized to that of untreated HeLa cells (Control). Nocodazole and paclitaxel are cytotoxic agents that interfere with microtubule polymerization and depolymerization, respectively, and are positive controls for delivery of anti-beta tubulin antibody. Error bars indicate mean ±s.d. (n=3); *p b 0.01 (t-test: two-sample assuming unequal variances).

Figure 8A:
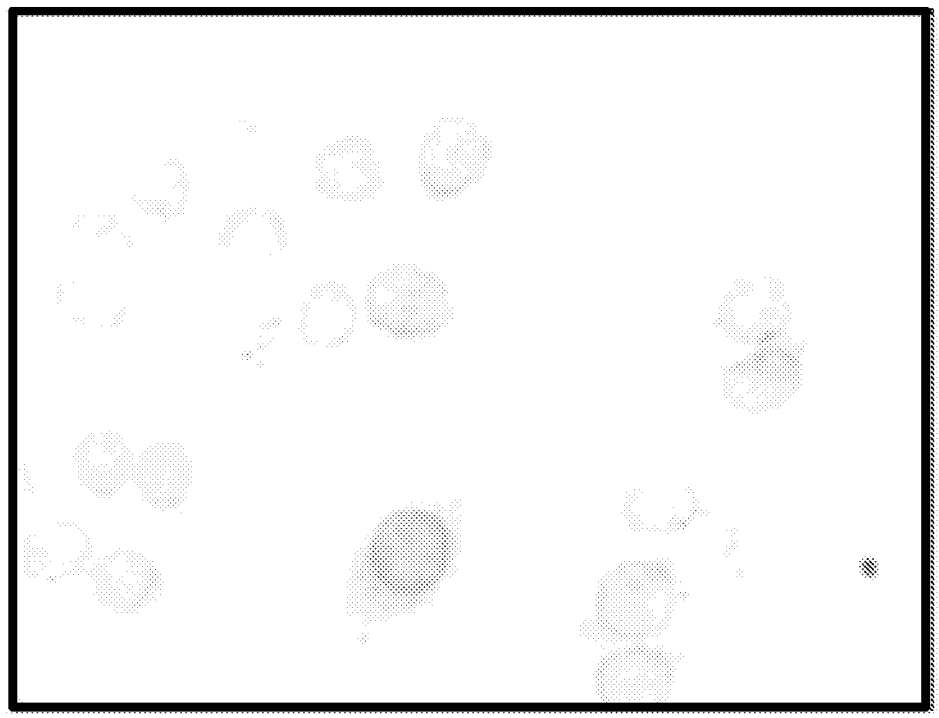
FIG. 8a illustrates microscopy fluorescence images demonstrating delivery of nuclear pore complex antibody.
Figure 8B:
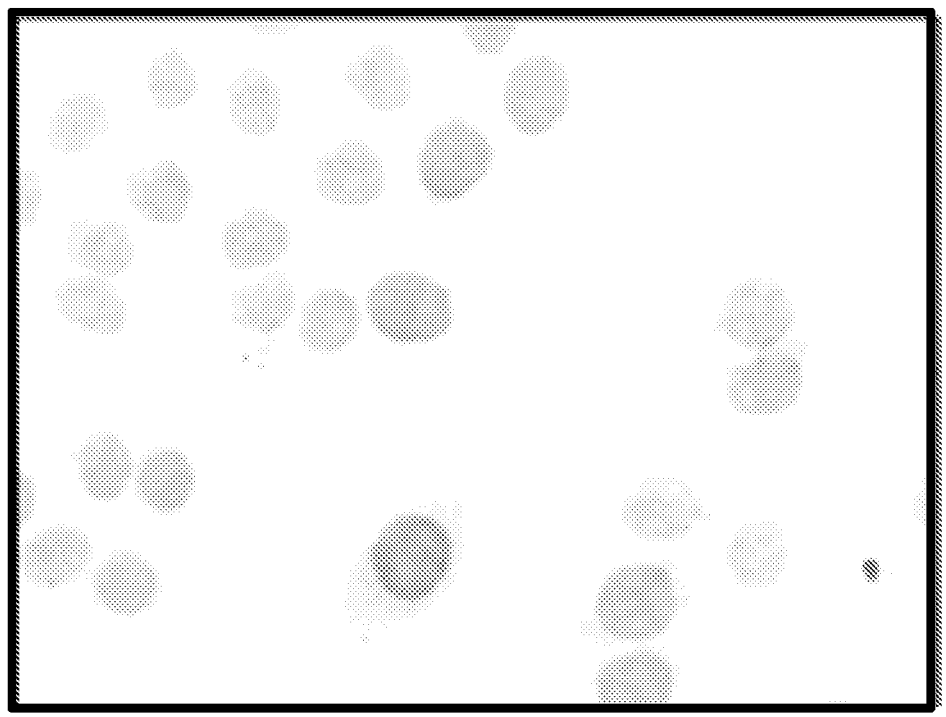
FIG. 8b illustrates microscopy fluorescence visualizing delivery of nuclear pore complex antibody and the cell nucleus.

In a different experiment, HeLa cells were incubated with 0.6 µM of mouse anti-NPC antibody with 0.2 µM of the Hex nanocarrier. After 24 h, cells were washed, fixed, permeabilized, and stained with goat anti-mouse IgG Alexa Fluor 647 conjugate as shown in FIG. 8a to visualize intracellular distribution of antibodies. Nuclei were then stained with Hoechst 33342 as shown in FIG. 8b.

Example 7 Intracellular Delivery of Antibody by Hex Nanocarrier Fused to Aurein Peptide The Aurein 1.2 sequence was appended to the C-terminus of H6-SPAB-Hex and to the N-terminus of Hex-SPAB-H6 such that the re-assembled Hex nanocarrier could have evenly distributed Aurein motifs opposite the SPAB domains. Fluorescently labeled $IgG_M$ was mixed with the Hex nanocarrier or the Au-Hex nanocarrier prior to incubation with HeLa cells. Cellular fluorescence was measured by flow cytometry to compare IgG uptake efficiency. Notably, $IgG_M$ carried by the Au-Hex nanocarrier showed internalization 4-fold higher than $IgG_M$ bound to the Hex nanocarrier at 5 h post-incubation, which was even greater than the maximum uptake of $IgG_M$ delivered by the Hex nanocarrier upon saturation at 24 h. HeLa cells were incubated for 24 h with 0.6 µM of mouse anti-NPC antibody and mixed with 0.2 µM of the Au-Hex nanocarrier or the Hex nanocarrier. Faster and greater uptake of $IgG_M$ carried by the Au-Hex nanocarrier was demonstrated in time-course fluorescence microscopy. Cellular fluorescence started to appear as early as 1 h after incubation for the Au-Hex nanocarrier. In contrast, no fluorescence was visible until 5 h incubation for the Hex nanocarrier.

Figure 9:
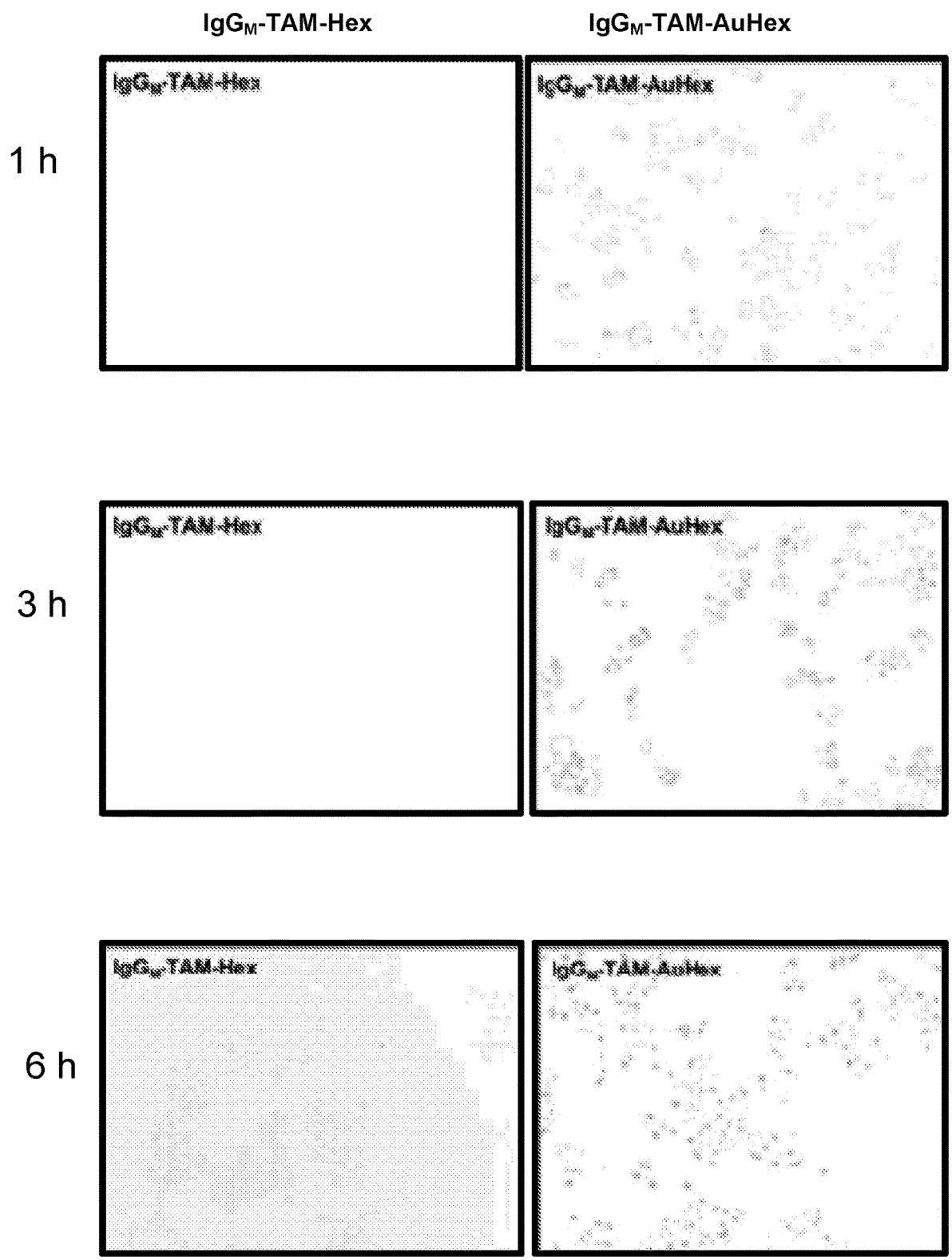
FIG. 9 illustrates microscopy fluorescence images demonstrating delivery of mouse antibodies labeled with TAM (IgG$_M$-TAM) bound to a nanocarrier (HEX or AuHEX) after 1 h, 3 h, and 6 h.
Figure 10:
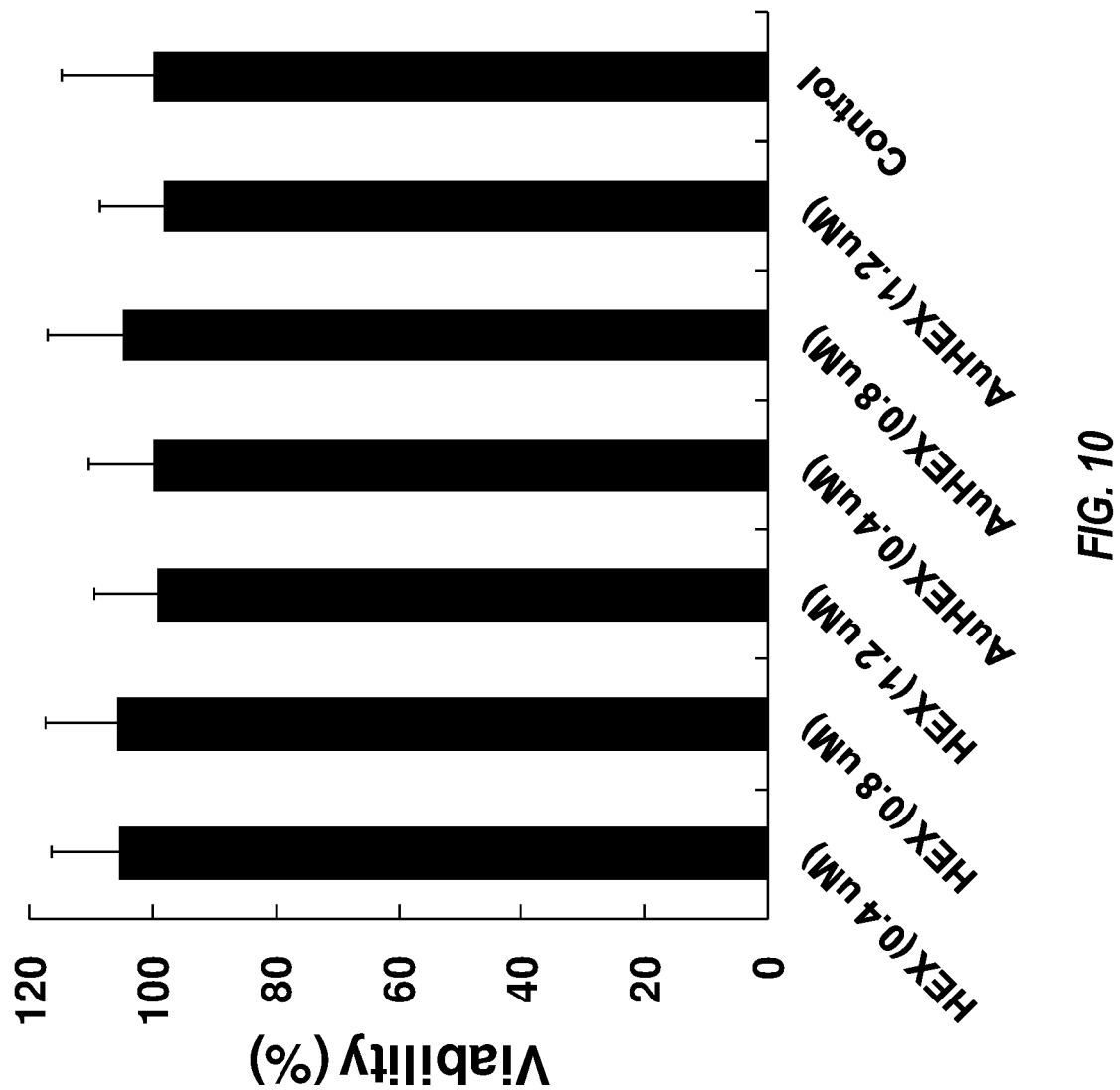
FIG. 10 illustrates a graph of cell viability under varying conditions in accordance with one or more embodiments of the disclosure.
Figure 11:
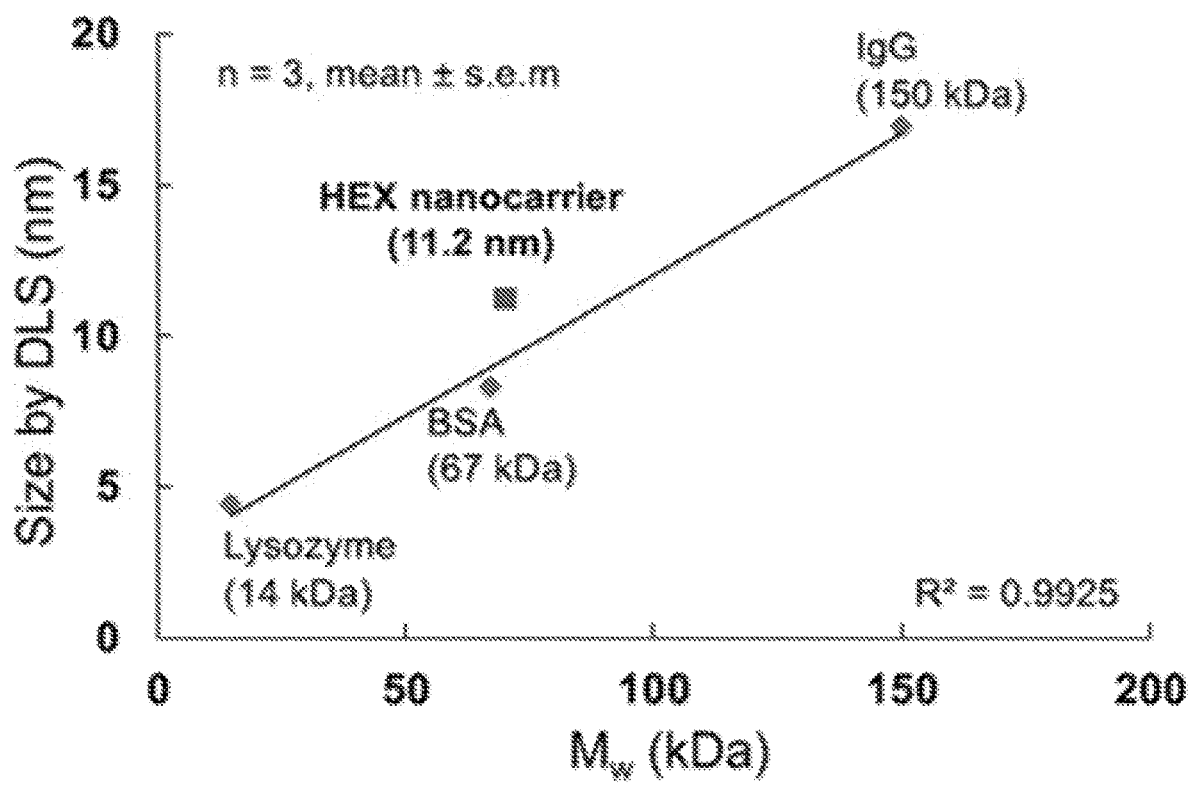
FIG. 11 illustrates a graph of size determined by Dynamic Light Scattering (DLS) against molecular weight ($M_W$) indicating a nanocarrier in accordance with an exemplary embodiment of the disclosure.
Figure 12A:
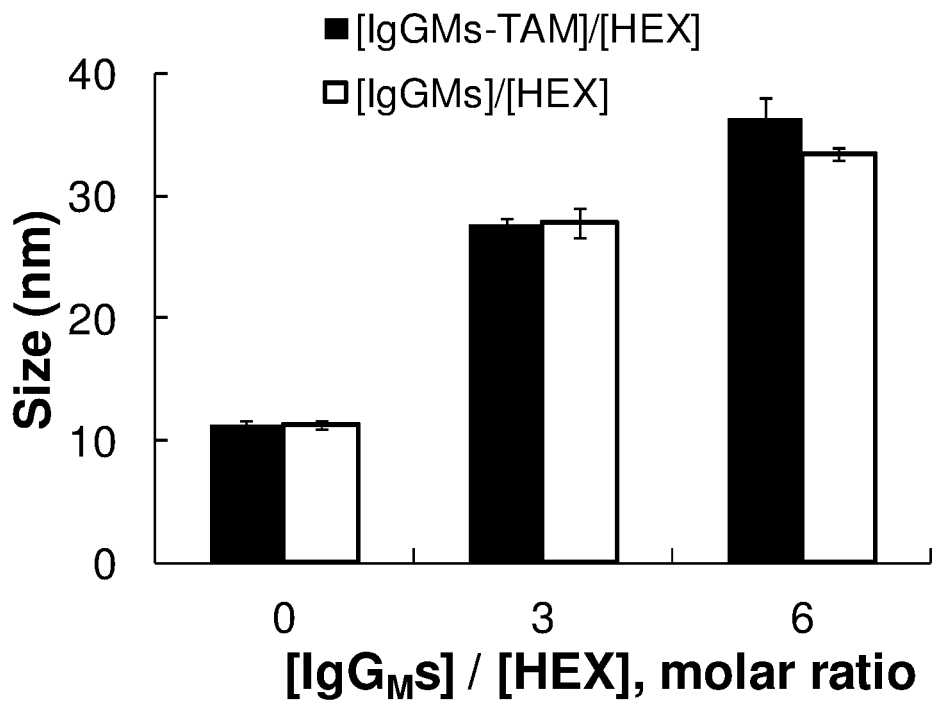
FIGS. 12a and 12b illustrate graphs displaying size of the antibody loaded nanocarrier at a ratio of mouse antibody (IgG$_M$) or rabbit antibody (IgG$_R$) to nanocarrier (HEX) of 0, 3, and 6 in accordance with an exemplary embodiment of the disclosure. The black bar shows size for antibody labeled with TAM.
Figure 12B:
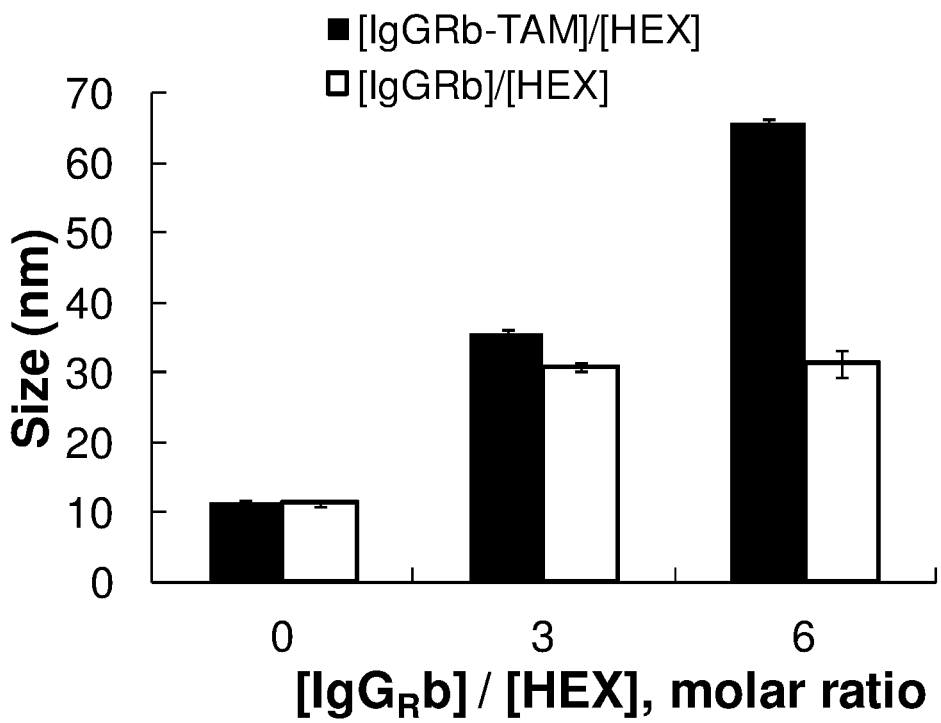

Fluorescence images were taken during a time course to demonstrate uptake of TAMRA-labeled $IgG_M$ as shown in FIG. 9. The delivery of $IgG_M$ was conducted at a fixed molar ratio of 3:1 $IgG_M$-TAM:Hex or Au-Hex, 0.4 µM $IgG_M$-TAM was mixed with the Hex or Au-Hex nanocarrier, and then incubated with HeLa cells at 37° C. Cellular fluorescence was imaged at various time points by fluorescence microscopy. Using the Au-Hex nanocarrier produced detectable fluorescence in about 1 h, while using the Hex nanocarrier produces detectable fluorescence after about 6 h as indicated in FIG. 9.

We claim:

1. An endocytic method of delivering a nanocarrier into a cell and to a target comprising:
   transporting a nanocarrier into a cell via endocytosis,
   wherein the nanocarrier comprises a core comprising a hexamer bundle domain comprising an alpha-helical protein comprising three or more coils and being approximately 11 nm in length; and the core is fused to a cargo comprising a protein; and
   wherein a target is located in the cytosol of the cell.

2. The method of claim 1, wherein a first bundle domain and a second bundle domain are the same.

3. The method of claim 2, wherein the first bundle domain and the second bundle domain are different.

4. The method of claim 1,
   wherein the cargo is fused to the bundle domain; and
   wherein the cargo is a therapeutic cargo.

5. The method of claim 4 further comprising releasing the cargo from the binding domain into the cytosol.

6. The method of claim 4, wherein the cargo is a designed ankyrin repeat protein (DARPin).

7. The method of claim 4, wherein the nanocarrier further comprises a linker.

8. The method of claim 7, wherein the linker comprises from about 2 to about 30 amino acid residues.

9. The method of claim 7,
   wherein one of:
      an N-terminus of the linker is fused to a C-terminus of the cargo; and a C-terminus of the linker is bound to an N-terminus of the core comprising an alpha-helical protein bundle domain; or
      an N-terminus of the linker is bound to a C-terminus of the core comprising an alpha-helical protein bundle domain; and a C-terminus of the linker is bound to an N-terminus of the cargo.

10. The method of claim 7, wherein the linker is selected from the group consisting of a glycine residue, a serine residue, a proline residue, and mixtures thereof.

11. The method of claim 4 further comprising increasing the uptake of the cargo in the cell utilizing a delivery enhancer.

12. The method of claim 11, wherein the delivery enhancer is selected from the group consisting of aurein and hexa-histidine.

13. The method of claim 4, wherein the nanocarrier further comprises a tag selected from the group consisting of His-tag, glutathione-S-transferase tag, FLAG tag, and myc-tag.

* * * * *